United States Patent [19]
Römer et al.

[11] Patent Number: 4,606,845
[45] Date of Patent: Aug. 19, 1986

[54] BICYCLOHEXYLETHANES

[75] Inventors: Michael Römer, Rodgau; Rudolf Eidenschink; Joachim Krause, both of Dieburg; Bernhard Scheuble, Alsbach-Hähnlein; Georg Weber, Erzhausen, all of Fed. Rep. of Germany

[73] Assignee: Merck Patent Gesellschaft mit beschrankter Haftung, Darmstadt, Fed. Rep. of Germany

[21] Appl. No.: 610,162

[22] Filed: May 14, 1984

[30] Foreign Application Priority Data

May 14, 1983 [DE] Fed. Rep. of Germany ....... 3317597

[51] Int. Cl.$^4$ ............ C09K 3/34; G02F 1/13; C07C 121/64; C07C 13/28; C07C 25/18; C07C 43/21; C07C 69/157; C07C 69/76
[52] U.S. Cl. ............ 252/299.63; 252/299.5; 560/102; 560/116; 560/117; 560/129; 560/138; 560/141; 570/129; 570/130; 570/182; 570/188; 568/591; 568/593; 568/609; 568/611; 568/612; 568/631; 568/659; 568/661; 568/664; 585/20; 350/350 R; 350/350 S; 558/411; 558/414; 558/426
[58] Field of Search ............ 252/299.5, 299.63; 350/350 R, 350 S; 260/464, 465 F, 465 G, 465 H, 465 C, 465 R; 560/102, 116, 117, 138, 141, 129; 585/20; 570/129, 130, 182, 188; 568/593, 591, 609, 611, 612, 631, 659, 661, 664

[56] References Cited

U.S. PATENT DOCUMENTS

| | | | |
|---|---|---|---|
| 4,035,056 | 7/1977 | Coates et al. | 252/299.66 |
| 4,261,651 | 4/1981 | Gray et al. | 252/299.63 |
| 4,340,498 | 7/1982 | Sugimori | 252/299.63 |
| 4,361,494 | 11/1982 | Osman et al. | 252/299.63 |
| 4,393,258 | 7/1983 | Sato et al. | 252/299.63 |
| 4,400,293 | 8/1983 | Romer et al. | 252/299.63 |
| 4,419,263 | 12/1983 | Praefcke et al. | 252/299.63 |
| 4,431,853 | 2/1984 | Sato et al. | 252/299.63 |
| 4,439,015 | 3/1984 | Rich et al. | 252/299.61 |
| 4,455,443 | 6/1984 | Takatsu et al. | 252/299.63 |
| 4,482,472 | 11/1984 | Carr et al. | 252/299.62 |
| 4,487,954 | 12/1984 | Sugimori et al. | 252/299.63 |
| 4,510,069 | 4/1985 | Eidenschink et al. | 252/299.63 |
| 4,514,044 | 4/1985 | Gunjima et al. | 252/299.63 |

FOREIGN PATENT DOCUMENTS

| | | | |
|---|---|---|---|
| 58981 | 9/1982 | European Pat. Off. | 252/299.63 |
| 84194 | 7/1983 | European Pat. Off. | 252/299.63 |
| 87032 | 8/1983 | European Pat. Off. | 252/299.63 |
| 103681 | 3/1984 | European Pat. Off. | 252/299.63 |
| 107116 | 5/1984 | European Pat. Off. | 252/299.63 |
| 3211601 | 10/1983 | Fed. Rep. of Germany | 252/299.63 |
| 3335550 | 4/1984 | Fed. Rep. of Germany | 252/299.63 |
| 57-54137 | 3/1982 | Japan | 252/299.63 |
| 57-59851 | 4/1982 | Japan | 252/299.63 |
| 58-8022 | 1/1983 | Japan | 252/299.63 |
| 58-8023 | 1/1983 | Japan | 252/299.63 |
| A8137642 | 8/1982 | United Kingdom | 252/299.63 |
| 2092169 | 8/1982 | United Kingdom | 252/299.63 |
| 2093057 | 8/1982 | United Kingdom | 252/299.63 |
| 2107733 | 5/1983 | United Kingdom | 252/299.6 |
| 2134110 | 8/1984 | United Kingdom | 252/299.63 |

OTHER PUBLICATIONS

Osman, M. A. et al., Mol. Cryst. Liq. Cryst., vol. 82, (Letters), pp. 339–344 (Jan. 1983).
Praefcke, V. K. et al., Chemiker-Zeitung., vol. 104, No. 9, pp. 269–271 (1980).

Primary Examiner—Teddy S. Gron
Attorney, Agent, or Firm—Millen and White

[57] ABSTRACT

New bicyclohexylethanes of formula I

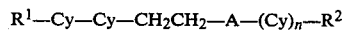

$$R^1-Cy-Cy-CH_2CH_2-A-(Cy)_n-R^2 \quad (I)$$

wherein $R^1$ is alkyl; $R^2$ is alkyl, in which one or two non-adjacent $CH_2$ groups can be replaced by O atoms, or is F, Cl, Br, CN, —COOalkyl or —O—CO-alkyl; or one of the radicals $R^1$ and $R^2$ can also be H; A is Cy, or 1,4-phenylene which is unsubstituted or substituted by one or two F and/or Cl atoms and/or $CH_3$ groups or by a CN group; Cy is 1,4-cyclohexylene and n is 0 or 1; the alkyl groups in each case containing 1–10 C atoms, with the proviso that n is 1 if A is Cy and $R^2$ is CN, can be used as constituents of dielectrics for electro-optical display elements.

14 Claims, No Drawings

BICYCLOHEXYLETHANES

BACKGROUND OF THE INVENTION

The present invention relates to new bicyclohexylethanes.

German Offenlegungsschrift No. 3,148,148 and European Offenlegungsschrift No. 0,056,501 give the general formula (1)

$$R^1-A^1-Z^1-(A^2-Z^2)_m-A^3-R^2 \qquad (1)$$

wherein $R^1$ can also be $CH_3(CH_2)_n-$, $A^1$ and $A^2$ can in each case also be Cy, $Z^1$ can also be a valency bond, $Z^2$ can also be $-CH_2CH_2-$, m can also be 1, $A^3$ can also be Cy or 1,4-phenylene, $R^2$ can also be $CH_3(CH_2)_n$, $CH_3(CH_2)_{n-2}COO-$, $CH_3(CH_2)_{n-2}O-CO-$ or $CH_3(CH_2)_{n-1}O-$ and n can be a number from zero to 11. These specifications also give the further general formula (2)

$$R^3-A^4-Z^3(A^5-Z^4)_p-A^6-CN \qquad (2)$$

in which $R^3$ can also be $CH_3(CH_2)_n-$, $A^4$ and $A^5$ in each case can also be Cy, $Z^3$ can also be a valency bond, $Z^4$ can also be $-CH_2CH_2-$, p can also be 1, $A^6$ can also be Cy or 1,4-phenylene and n can be a number from zero to 11. However, neither subformulae nor individual compounds which contain the $-CH_2CH_2-$ group, as do the bicyclohexylethanes of the present formula I, are mentioned therein. Compared with the two publications mentioned, these compounds are therefore still new, and they are not suggested by the prior art as stated by the two publications mentioned.

SUMMARY OF THE INVENTION

It is an object of this invention to provide new, stable liquid crystalline or mesogenic compounds useful in liquid crystalline dielectrics.

Upon further study of the specification and appended claims, further objects and advantages of this invention will become apparent to those skilled in the art.

These objects have been attained by providing new compounds of the formula I $$R^1-Cy-Cy-CH_2CH_2-A-(Cy)_n-R^2 \qquad I$$

wherein $R^1$ is alkyl; $R^2$ is alkyl, in which one or two non-adjacent $CH_2$ groups can be replaced by O atoms, or is F, Cl, Br, CN, $-COOalkyl$ or $-O-CO-alkyl$; and one of the radicals $R^1$ and $R^2$ can also be H; A is Cy, or 1,4-phenylene which is unsubstituted or substituted by one or two F and/or Cl atoms and/or $CH_3$ groups or by a CN group; Cy is 1,4-cyclohexylene; and n is 0 or 1; the alkyl groups in each case containing 1-10 C atoms; with the proviso that n is 1 if A is Cy and $R^2$ is CN.

For simplicity, "Phe" in the following text is a 1,4-phenylene radical, it being possible for this radical to be unsubstituted or substituted by one or two fluorine and/or chlorine atoms and/or $CH_3$ groups or by a CN group.

DETAILED DISCUSSION

Like similar compounds, for example like the compounds known from German Offenlegungsschrift No. 3,225,290, the compounds of the formula I can be used as components of liquid crystal dielectrics, in particular for displays which are based on the principle of the twisted cell, the guest-host effect, the effect of deformation of orientated phases or the effect of dynamic scattering.

It has been found that the compounds of the formula I are outstandingly suitable as components of liquid crystal dielectrics. In particular, stable liquid crystal phases with a wide liquid crystal range and low viscosity, in particular phases which are also liquid crystal and of low viscosity at low temperatures, can be prepared with the aid of these compounds.

Furthermore, by providing the compounds of the formula I, the range of liquid crystal substances which are suitable for the preparation of liquid crystal mixtures from various technological points of view is quite generally substantially increased.

The compounds of the formula I have a wide field of application. Depending on the choice of substituents, these compounds can be used as base materials, from which liquid crystal dielectrics are predominantly composed; however, it is also possible to add compounds of the formula I to liquid crystal base materials consisting of other classes of compounds, for example in order to reduce the viscosity or the birefringence of such a dielectric and/or to increase its clear point. The compounds of the formula I, especially those containing cyclohexane rings with substituents in cis-positions, and those wherein $R^2$ is H, Cl or Br, are furthermore suitable as intermediates for the preparation of other substances which can be used as constituents of liquid crystal dielectrics.

The compounds of the formula I are colorless in the pure state and form liquid crystal mesophases of low viscosity in a temperature range favorably located for electrooptical use. Chemically, they are very stable.

The invention thus relates to the compounds of the formula I and to a process for their preparation, characterized in that a compound which otherwise corresponds to the formula I but contains one or more reducible group(s) and/or C—C bond(s) instead of H atoms, is treated with a reducing agent, or in that, for the preparation of esters of the formula I (wherein $R^2$ is $-COOalkyl$ or $-O-COalkyl$), a corresponding carboxylic acid or one of its reactive derivatives is reacted with a corresponding alcohol or phenol or one of its reactive derivatives, or in that, for the preparation of halogen derivatives of the formula I (wherein $R^2$ is F, Cl or Br and or A is 1,4-phenylene which is substituted by one or two F and/or Cl atoms) with aromatically bonded halogen, a corresponding amino compound is diazotized and the diazonium group is then replaced by a fluorine, chlorine or bromine atom by methods which are known per se, or in that, for the preparation of nitriles of the formula I ($R^2$=CN), a corresponding carboxylic acid amide is dehydrated or a corresponding carboxylic acid halide is reacted with sulfamide, or in that, for the preparation of ethers of the formula I (wherein $R^2$ is an alkyl group in which one or two $CH_2$ groups are replaced by O atoms), a corresponding hydroxy compound is etherified, and/or in that, if appropriate, a chlorine or bromine compound of the formula I (wherein $R^2$ is Cl or Br and/or wherein A denotes a 1,4-phenylene radical which is substituted by one or two Cl atoms) is reacted with a cyanide.

The invention also relates to the use of the compounds of the formula I as components of liquid crystal dielectrics. The invention furthermore relates to liquid crystal dielectrics containing at least one compound of the formula I, and electrooptical display elements containing such dielectrics.

$R^1$, $R^2$, A, Cy, Phe and n have, above and below, the meaning given, unless expressly indicated otherwise.

The compounds of the formula I accordingly include compounds of the part formulae Ia to Id:

$R^1$—Cy—Cy—CH$_2$CH$_2$—Cy—$R^2$    Ia $R^1$—Cy—Cy—CH$_2$CH$_2$—Phe—$R^2$    Ib $R^1$—Cy—Cy—CH$_2$CH$_2$—Cy—CY—$R^2$    Ic $R^1$—Cy—Cy—CH$_2$CH$_2$—Phe—Cy—$R^2$    Id

Of these, those of the formulae Ia and Ib are preferred.

In the compounds of the formula I and Ia to Id, the alkyl radicals, wherein, in the case of $R^2$, one or two non-adjacent CH$_2$ groups can also be replaced by O atoms, can be straight-chain or branched. Preferably, they are straight-chain and have 2, 3, 4, 5, 6 or 7 C atoms, and accordingly are preferably ethyl, propyl, butyl, pentyl, hexyl and heptyl, and in the case of $R^2$ also ethoxy, propoxy, butoxy, pentoxy, hexoxy, heptoxy, methoxymethyl, ethoxymethyl, propoxymethyl, methoxymethoxy and ethoxymethoxy, and furthermore methyl, octyl, nonyl, decyl, methoxy, octoxy, nonoxy or decoxy.

Compounds of the formula I and Ia to Id with branched end groups $R^1$ and/or $R^2$ may sometimes be of importance because of their better solubility in the usual liquid crystal base materials, but in particular as chiral doping substances, if they are optically active. Branched groups of this type as a rule contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl and 2-heptylpentyl, and for $R^2$ also isopropoxy, 2-methyl-pentoxy, 3-methylpentoxy, 2-ethylhexoxy, 1-methylhexoxy and 1-methylheptoxy.

Specifically, $R^2$ is preferably alkyl, alkoxy or CN, A is preferably Cy or unsubstituted 1,4-phenylene and n is preferably 0. Of the compounds of the formulae I and Ia to Id, those in which at least one of the radicals contained therein has one of the preferred meanings mentioned are preferred. Particularly preferred smaller groups of compounds are those of the formulae Ie to Ih:

$R^1$—Cy—Cy—CH$_2$CH$_2$—Cy—alkyl    Ie $R^1$—Cy—Cy—CH$_2$CH$_2$—Phe—alkYl    If $R^1$—Cy—Cy—Ch$_2$CH$_2$—Phe—alkoxy    Ig $R^1$—Cy—Cy—CH$_2$CH$_2$—Phe—CN    Ih In the compounds of the formulae I and Ia to Ih, those stereoisomers wherein the substituents on the cyclohexylene radicals are in each case in the trans-position relative to one another are preferred.

The compounds of the formula I are prepared by methods which are known per se, such as those described in the literature (for example in standard works such as Houben-Weyl, Methoden der Organischen Chemie [Methods of Organic Chemistry], Georg-Thieme Verlag, Stuttgart), and in particular under reaction conditions which are known and suitable for the reactions mentioned. Variants which are known per se and are not mentioned here in more detail can also be utilized.

If desired, the starting substances can also be formed in situ, such that they are not isolated from the reaction mixture but are immediately reacted further to give the compounds of the formula I.

The compounds of the formula I are preferably prepared by reducing a compound which otherwise corresponds to the formula I but contains one or more reducible groups and/or C—C bonds instead of H atoms.

Preferred possible reducible groups are carbonyl groups, in particular keto groups, and furthermore, for example, free or esterified hydroxyl groups or aromatically bonded halogen atoms. Preferred starting substances for the reduction correspond to the formula I, but contain one of the groups —CO—CH$_2$—, —CH$_2$—CO— or —CH=CH— instead of the —CH$_2$CH$_2$— group and/or a cyclohexane ring instead of a cyclohexane ring.

Examples of preferred starting substances for the reduction are ketones of the formulae $R^1$—Cy—Cy—CH$_2$—CO—A—(Cy)$_n$—$R^2$ and $R^1$—Cy—Cy—CO—CH$_2$—A—(Cy)$_n$—$R^2$, but in particular $R^1$—Cy—Cy—CH$_2$—CO—Phe—(Cy)$_n$—$R^2$.

The ketones last mentioned can be obtained, for example, by a Friedel-Crafts reaction from the corresponding aromatics of the formula H—Phe—(Cy)$_n$—$R^2$ with the corresponding acid chlorides of the formula $R^1$—Cy—Cy—CH$_2$—CO—Cl.

Examples of starting substances with cyclohexene rings are those of the formula

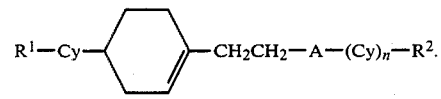

These can be obtained, for example, by reacting 4-$R^1$—Cy-cyclohexanones with organometallic compounds of the formula LiCH$_2$CH$_2$—A—(Cy)$_n$—$R^2$ or corresponding Grignard compounds and subsequently dehydrating the resulting carbinols.

Other preferred starting substances correspond to the formula

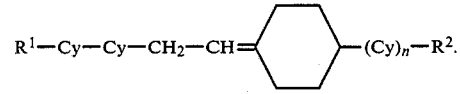

These can be obtained, for example, by a Wittig reaction from bromides of the formula $R^1$—Cy—Cy—CH$_2$—CH$_2$—Br with triphenylphosphine, and then with 4—$R^2$—(Cy)$_n$—cyclohexanones.

The reduction is preferably carried out by catalytic hydrogenation at temperatures between about 0° and about 200° under pressures between about 1 and about 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane.

Preferred suitable catalysts are noble metals, such as Pt or Pd, which can be used in the form of oxides (for example PtO$_2$ or PdO), on a carrier (for example Pd-oncharcoal, -calcium carbonate or -strontium carbonate) or in finely divided form. The ketones mentioned can also be reduced by the methods of Clemmensen (with zinc, zinc amalgam or tin and hydrochloric acid, preferably in aqueous-alcoholic solution or in a heterogeneous phase system with water/benzene or water/toluene at temperatures between about 80° and 120°) or Wolff-Kishner (with hydrazine) preferably in the presence of alkali, such as KOH or NaOH, in a high-boiling solvent, such as diethyleneglycol or triethyleneglycol, at temperatures between about 100° and 200°).

Starting substances of the formula $R^1$—Cy—Cy—CH=CH—Phe—$(Cy)_n$—$R^2$, which can be obtained, for example, by a Wittig reaction from bromides of the formula $R^1$—Cy—Cy—$CH_2Br$ and aldehydes of the formula O=CH—Phe—$(Cy)_n$—$R^2$, can also be reduced with $NaBH_4$, preferably in an inert solvent, such as methanol, ethanol or diglyme, at temperatures between about 0° and 120°.

Esters of the formula I (wherein $R^2$ is —COOalkyl or —O—CO—alkyl) can also be obtained by esterification of corresponding carboxylic acids of the formula $R^3$—COOH [wherein $R^3$ is (a) $R^1$—Cy—Cy—$CH_2CH_2$—A—$(Cy)_n$— or (b) alkyl] (or reactive derivatives thereof) with alcohols or phenols of the formula $R^4$—OH [wherein $R^4$ in the case of (a) is alkyl and in the case of (b) is $R^1$—Cy—Cy—$CH_2CH_2$—A—$(Cy)_n$—] (or reactive derivatives thereof).

Particularly suitable reactive derivatives of the carboxylic acids mentioned are the acid halides, especially the chlorides and bromides, and furthermore the anhydrides, for example also mixed anhydrides of the formula $R^3$—CO—O—CO—$CH_3$, azides or esters, in particular alkyl esters with 1-4 C atoms in the alkyl group.

Possible reactive derivatives of the alcohols or phenols mentioned are, in particular, the corresponding metal alcoholates or phenolates of the formula $R^4$—OM, in which M is one equivalent or a metal, preferably an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as dimethylformamide (DMF) or phosphoric acid hexamethyltriamide, hydrocarbons, such as carbon tetrachloride or tetrachloroethylene, and sulfoxides, such as dimethylsulfoxide or sulfolane. Water-immiscible solvents can at the same time advantageously be used for removal of the water formed during the esterification by azeotropic distillation. An excess of an organic base, for example pyridine, quinoline or triethylamine, can sometimes also be used as the solvent for the esterification.

The esterification can also be carried out in the absence of a solvent, for example by simply heating the components in the presence of sodium acetate. The reaction temperature is usually between −50° and +250°, preferably between −20° and +80°. At these temperatures, the esterification reactions have as a rule ended after 15 minutes to 48 hours.

Specifically, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, the important bases being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification consists in first converting the alcohol or the phenol into the sodium or potassium alcoholate or phenolate, for example by treatment with ethanolic sodium hydroxide solution or potassium hydroxide solution, isolating this alcoholate or phenolate and suspending it in acetone or diethyl ether, together with sodium bicarbonate or potassium carbonate, with stirring, and adding a solution of the acid chloride or anhydride in diethyl ether, acetone or DMF to this suspension, preferably at temperatures between about −25° and +20°.

Halogen derivatives of the formula I (wherein $R^2$ is F, Cl or Br and/or A is 1,4-phenylene which is substituted by one or two F and/or Cl atoms) with aromatically bonded halogen can be prepared from the corresponding amines by the methods of the Schiemann reaction (compare, for example, The Merck Index, 9th Edition, Merck & Co., Inc., Rahway, N.J., USA, 1976, page ONR-80) or the Sandmeyer reaction (compare, for example, The Merck Index, Loc.cit., page ONR-79).

The diazotization is preferably effected first with a salt or an ester of nitrous acid (such as $NaNO_2$ or butyl nitrite), in an aqueous-acid phase, it being possible to use, for example, HF, HCl, HBr, $H_2SO_4$ or $HBF_4$ as the acid, at temperatures between about −20° and +10°. An additional inert solvent may be present, for example an ether, such as THF or dioxane, or a hydrocarbon, such as toluene or xylene.

To prepare the fluorine compounds of the formula I (wherein $R^2$ is F and/or A is 1,4-phenylene which is substituted by one or two F atoms), the diazotization is preferably carried out in $HBF_4$. The diazonium tetrafluoborates are thereby formed, and these can already be decomposed at temperatures between about 10° and 100°. If the diazotization is carried out with $NaNO_2$ in anhydrous HF, the desired fluorine compound is obtained directly by subsequent warming.

A replacement of the diazonium group by Cl or Br is preferably carried out in aqueous solution in the presence of $Cu_2Cl_2$ or $Cu_2Br_2$ at temperatures between 30° and 100°.

To prepare nitriles of the formula I ($R^2$=CN and or A=1,4-phenylene which is substituted by a CN group), in particular those of the formula Ih, corresponding acid amides, for example those of the formula $R^1$—Cy—Cy—$CH_2CH_2$—A—$(Cy)_n$—$CONH_2$, can be dehydrated. The amides can be obtained, for example, from corresponding esters or acid halides by reaction with ammonia. Examples of suitable agents which split off water are inorganic acid chlorides, such as $SOCl_2$, $PCl_3$, $PCl_5$, $POCl_3$, $SO_2Cl_2$ and $COCl_2$, and furthermore $P_2O_5$, $P_2S_5$, $AlCl_3$ (for example as a double compound with NaCl), aromatic sulfonic acids and sulfonic acid halides. This reaction can be carried out in the presence or absence of an inert solvent at temperatures between about 0° and 150°; examples of possible solvents are bases, such as pyridine or triethylamine, aromatic hydrocarbons, such as benzene, toluene or xylene, or amides, such as DMF.

Alkoxy compounds of the formula I ($R^2$=alkoxy) can be obtained by alkylation of corresponding hydroxy compounds, preferably corresponding phenols, the hydroxy compound preferably first being converted into a corresponding metal derivative, for example into the corresponding alkali metal alcoholate or alkali metal phenolate by treatment with NaOH, KOH, $Na_2CO_3$ or $K_2CO_3$. This can then be reacted with the corresponding alkyl halide or sulfonate or dialkyl sulfate, preferably in an inert solvent, such as acetone, DMF or dimethylsulfoxide, or an excess of aqueous or aqueous-alcoholic NaOH or KOH at temperatures between about 20° and 100°.

To prepare the nitriles, it is also possible to react corresponding chlorine or bromine compounds with a cyanide, preferably with a metal cyanide, such as NaCN, KCN or $Cu_2(CN)_2$, for example in the presence of pyridine in an inert solvent, such as DMF or N-methylpyrrolidone, at temperatures between 20° and 200°.

To prepare the abovementioned nitriles, it is also possible to react corresponding acid halides, preferbly the chlorides, with sulfamide, preferably in an inert solvent, such as tetramethylene sulfone, at temperatures between about 80° and 150°, preferably at about 120°. After customary working up, the nitriles can be isolated directly.

The dielectrics according to the invention comprise 2 to 15, preferably 3 to 12, components, at least one of which is a compound of the formula I. The other constituents are preferably chosen from the nematic or nematogenic substances, in particular the known substances from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyl-dioxanes, optionally halogenated stilbenes, benzyl phenyl ethers, tolanes and substituted cinnamic acids.

The most important compounds which can be used as constituents of such liquid crystal dielectrics can be characterized by the formula III $$R^5—L—G—E—R^6 \qquad III$$

wherein L and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| | |
|---|---|
| —CH=CH— | —N(O)=N— |
| —CH=CY— | —CH=N(O)— |
| —C≡C—. | —CH₂—CH₂— |
| —CO—O— | —CH₂—O— |
| —CO—S— | —CH₂—S— |
| —CH=N— | —COO—Phe—COO— | or a C—C single bond, Y is halogen, preferably chlorine, or —CN, and $R^5$ and $R^6$ are alkyl, alkoxy, alkanoyloxy or alkoxycarbonyloxy with up to 18, preferably up to 8, carbon atoms, or one of these radicals is also CN, NC, $NO_2$, $CF_3$, F, Cl or Br.

In most of these compounds, $R^5$ and $R^6$ differ from one another, one of these radicals usually being an alkyl or alkoxy group. However, other variants of the envisaged substituents are also usual. Many such substances or mixtures thereof are commercially available.

The dielectrics according to the invention contain about 1 to 60%, preferably 5 to 40%, of one or more compounds of the formula I.

The dielectrics according to the invention are prepared in a manner which is customary per se. As a rule, the components are dissolved in one another, preferably at elevated temperature.

The liquid crystal dielectrics according to the invention can be modified by suitable additives such that they can be used in all the types of liquid crystal display elements as yet disclosed.

Such additives are known to the expert and are described in detail in the literature. For example, conductive salts, preferably ethyl-dimethyl-dodecyl-ammonium 4-hexyloxybenzoate, tetrabutylammonium tetraphenylboronate or complex salts of crown ethers (compare, for example, I. Haller et al., Mol. Cryst. Liq. Cryst. Volume 24, pages 249–258 (1973)) can be added to improve the conductivity, dichroic dyestuffs can be added to produce colored guest-host systems or substances can be added to modify the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

"Customary working up" means: water is added, the mixture is extracted with methylene chloride, the organic phase is separated off, dried and evaporated and the resulting product is purified, if necessary, by chromatography on silica gel.

EXAMPLE 1

A mixture of 36.8 g of trans/trans-4-p-propylbenzoyl-methyl-4'-propyl-bicyclohexyl (obtainable by reduction of trans/trans-4'-propyl-bicyclohexyl-4-carboxylic acid to trans/trans-4-hydroxymethyl-4'-propyl-bicyclohexyl with LiAlH$_4$, conversion of the product into the tosylate, reaction with KCN to give trans/trans-4-cyanomethyl-4'-propyl-bicyclohexyl, hydrolysis to the carboxylic acid, reaction with SOCl$_2$ to give the acid chloride and reaction with propylbenzene in the presence of AlCl$_3$), 30 g of KOH, 50 ml of 85% hydrazine and 500 ml of triethylene glycol is warmed at 120° for 1 hour. The temperature is slowly increased until the hydrazone formed decomposes, and the mixture is boiled for a further 4 hours, cooled and worked up in the customary manner to give trans/trans-4-(2-p-propylphenyl-ethyl)-4'-propyl-bicyclohexyl, m.p. 34°, c.p. 158°.

The following compounds are obtained analogously by reduction of corresponding ketones:

trans/trans-4-(2-p-phenyl-ethyl)-4'-propyl-bicyclohexyl
trans/trans-4-(2-p-tolyl-ethyl)-4'-propyl-bicyclohexyl
trans/trans-4-(2-p-ethylphenyl-ethyl)-4'-ethyl-bicyclohexyl
trans/trans-4-(2-p-ethylphenyl-ethyl)-4'-propyl-bicyclohexyl
trans/trans-4-(2-p-ethylphenyl-ethyl)-4'-butyl-bicyclohexyl
trans/trans-4-(2-p-ethylphenyl-ethyl)-4'-pentyl-bicyclohexyl
trans/trans-4-(2-p-ethylphenyl-ethyl)-4'-hexyl-bicyclohexyl
trans/trans-4-(2-p-ethylphenyl-ethyl)-4'-heptyl-bicyclohexyl
trans/trans-4-(2-p-propylphenyl-ethyl)-4'-ethyl-bicyclohexyl
trans/trans-4-(2-p-propylphenyl-ethyl)-4'-butyl-bicyclohexyl
trans/trans-4-(2-p-propylphenyl-ethyl)-4'-pentyl-bicyclohexyl
trans/trans-4-(2-p-propylphenyl-ethyl)-4'-hexyl-bicyclohexyl
trans/trans-4-(2-p-propylphenyl-ethyl)-4'-heptyl-bicyclohexyl
trans/trans-4-(2-p-butylphenyl-ethyl)-4'-ethyl-bicyclohexyl
trans/trans-4-(2-p-butylphenyl-ethyl)-4'-propyl-bicyclohexyl
trans/trans-4-(2-p-butylphenyl-ethyl)-4'-butyl-bicyclohexyl
trans/trans-4-(2-p-butylphenyl-ethyl)-4'-pentyl-bicyclohexyl
trans/trans-4-(2-p-butylphenyl-ethyl)-4'-hexyl-bicyclohexyl
trans/trans-4-(2-p-butylphenyl-ethyl)-4'-heptyl-bicyclohexyl
trans/trans-4-(2-p-pentylphenyl-ethyl)-4'-ethyl-bicyclohexyl
trans/trans-4-(2-p-pentylphenyl-ethyl)-4'-propyl-bicyclohexyl
trans/trans-4-(2-p-pentylphenyl-ethyl)-4'-butyl-bicyclohexyl
trans/trans-4-(2-p-pentylphenyl-ethyl)-4'-pentyl-bicyclohexyl
trans/trans-4-(2-p-pentylphenyl-ethyl)-4'-hexyl-bicyclohexyl
trans/trans-4-(2-p-pentylphenyl-ethyl)-4'-heptyl-bicyclohexyl
trans/trans-4-(2-p-hexylphenyl-ethyl)-4'-ethyl-bicyclohexyl
trans/trans-4-(2-p-hexylphenyl-ethyl)-4'-propyl-bicyclohexyl
trans/trans-4-(2-p-hexylphenyl-ethyl)-4'-butyl-bicyclohexyl
trans/trans-4-(2-p-hexylphenyl-ethyl)-4'-pentyl-bicyclohexyl
trans/trans-4-(2-p-hexylphenyl-ethyl)-4'-hexyl-bicyclohexyl
trans/trans-4-(2-p-hexylphenyl-ethyl)-4'-heptyl-bicyclohexyl
trans/trans-4-(2-p-heptylphenyl-ethyl)-4'-ethyl-bicyclohexyl
trans/trans-4-(2-p-heptylphenyl-ethyl)-4'-propyl-bicyclohexyl
trans/trans-4-(2-p-heptylphenyl-ethyl)-4'-butyl-bicyclohexyl
trans/trans-4-(2-p-heptylphenyl-ethyl)-4'-pentyl-bicyclohexyl
trans/trans-4-(2-p-heptylphenyl-ethyl)-4'-hexyl-bicyclohexyl
trans/trans-4-(2-p-heptylphenyl-ethyl)-4'-heptyl-bicyclohexyl
trans/trans-4-(2-p-methoxymethylphenyl-ethyl)-4'-ethylbicyclohexyl
trans/trans-4-(2-p-methoxymethylphenyl-ethyl)-4'-propylbicyclohexyl
trans/trans-4-(2-p-methoxymethylphenyl-ethyl)-4'-butylbicyclohexyl
trans/trans-4-(2-p-methoxymethylphenyl-ethyl)-4'-pentylbicyclohexyl
trans/trans-4-(2-p-methoxymethylphenyl-ethyl)-4'-hexylbicyclohexyl
trans/trans-4-(2-p-methoxymethylphenyl-ethyl)-4'-heptylbicyclohexyl
trans/trans-4-(2-p-methoxyphenyl-ethyl)-4'-ethyl-bicyclohexyl
trans/trans-4-(2-p-methoxyphenyl-ethyl)-4'-propyl-bicyclohexyl
trans/trans-4-(2-p-methoxyphenyl-ethyl)-4'-butyl-bicyclohexyl
trans/trans-4-(2-p-methoxyphenyl-ethyl)-4'-pentyl-bicyclohexyl
trans/trans-4-(2-p-methoxyphenyl-ethyl)-4'-hexyl-bicyclohexyl
trans/trans-4-(2-p-methoxyphenyl-ethyl)-4'-heptyl-bicyclohexyl
trans/trans-4-(2-p-ethoxyphenyl-ethyl)-4'-ethyl-bicyclohexyl
trans/trans-4-(2-p-ethoxyphenyl-ethyl)-4'-propyl-bicyclohexyl
trans/trans-4-(2-p-ethoxyphenyl-ethyl)-4'-butyl-bicyclohexyl
trans/trans-4-(2-p-ethoxyphenyl-ethyl)-4'-pentyl-bicyclohexyl
trans/trans-4-(2-p-ethoxyphenyl-ethyl)-4'-hexyl-bicyclohexyl
trans/trans-4-(2-p-ethoxyphenyl-ethyl)-4'-heptyl-bicyclohexyl
trans/trans-4-(2-p-propoxyphenyl-ethyl)-4'-ethyl-bicyclohexyl
trans/trans-4-(2-p-propoxyphenyl-ethyl)-4'-propyl-bicyclohexyl
trans/trans-4-(2-p-propoxyphenyl-ethyl)-4'-butyl-bicyclohexyl trans/trans-4-(2-p-propoxyphenyl-ethyl)-4'-pentyl-bicyclohexyl
trans/trans-4-(2-p-propoxyphenyl-ethyl)-4'-hexyl-bicyclohexyl
trans/trans-4-(2-p-propoxyphenyl-ethyl)-4'-heptyl-bicyclohexyl
trans/trans-4-(2-p-butoxyphenyl-ethyl)-4'-ethyl-bicyclohexyl
trans/trans-4-(2-p-butoxyphenyl-ethyl)-4'-propyl-bicyclohexyl
trans/trans-4-(2-p-butoxyphenyl-ethyl)-4'-butyl-bicyclohexyl
trans/trans-4-(2-p-butoxyphenyl-ethyl)-4'-pentyl-bicyclohexyl
trans/trans-4-(2-p-butoxyphenyl-ethyl)-4'-hexyl-bicyclohexyl
trans/trans-4-(2-p-butoxyphenyl-ethyl)-4'-heptyl-bicyclohexyl
trans/trans-4-(2-p-methoxymethoxyphenyl-ethyl)-4'-ethyl-bicyclohexyl
trans/trans-4-(2-p-methoxymethoxyphenyl-ethyl)-4'-propyl-bicyclohexyl
trans/trans-4-(2-p-methoxymethoxyphenyl-ethyl)-4'-butyl-bicyclohexyl
trans/trans-4-(2-p-methoxymethoxyphenyl-ethyl)-4'-pentyl-bicyclohexyl
trans/trans-4-(2-p-methoxymethoxyphenyl-ethyl)-4'-hexyl-bicyclohexyl
trans/trans-4-(2-p-methoxymethoxyphenyl-ethyl)-4'-heptyl-bicyclohexyl
trans/trans-4-[2-p-(trans-4-ethylcyclohexyl)-phenylethyl]-4'-ethyl-bicyclohexyl
trans/trans-4-[2-p-(trans-4-ethylcyclohexyl)-phenylethyl]-4'-propyl-bicyclohexyl
trans/trans-4-[2-p-(trans-4-ethylcyclohexyl)-phenylethyl]-4'-butyl-bicyclohexyl
trans/trans-4-[2-p-(trans-4-ethylcyclohexyl)-phenylethyl]-4'-pentyl-bicyclohexyl
trans/trans-4-[2-p-(trans-4-ethylcyclohexyl)-phenylethyl]-4'-hexyl-bicyclohexyl
trans/trans-4-[2-p-(trans-4-ethylcyclohexyl)-phenylethyl]-4'-heptyl-bicyclohexyl
trans/trans-4-[2-p-(trans-4-propylcyclohexyl)-phenylethyl]-4'-ethyl-bicyclohexyl
trans/trans-4-[2-p-(trans-4-propylcyclohexyl)-phenylethyl]-4'-propyl-bicyclohexyl
trans/trans-4-[2-p-(trans-4-propylcyclohexyl)-phenylethyl]-4'-butyl-bicyclohexyl
trans/trans-4-[2-p-(trans-4-propylcyclohexyl)-phenylethyl]-4'-pentyl-bicyclohexyl
trans/trans-4-[2-p-(trans-4-propylcyclohexyl)-phenylethyl]-4'-hexyl-bicyclohexyl
trans/trans-4-[2-p-(trans-4-propylcyclohexyl)-phenylethyl]-4'-heptyl-bicyclohexyl
trans/trans-4-[2-p-(trans-4-butylcyclohexyl)-phenylethyl]-4'-ethyl-bicyclohexyl
trans/trans-4-[2-p-(trans-4-butylcyclohexyl)-phenylethyl]-4'-propyl-bicyclohexyl
trans/trans-4-[2-p-(trans-4-butylcyclohexyl)-phenylethyl]-4'-butyl-bicyclohexyl
trans/trans-4-[2-p-(trans-4-butylcyclohexyl)-phenylethyl]-4'-pentyl-bicyclohexyl
trans/trans-4-[2-p-(trans-4-butylcyclohexyl)-phenylethyl]-4'-hexyl-bicyclohexyl
trans/trans-4-[2-p-(trans-4-butylcyclohexyl)-phenylethyl]-4'-heptyl-bicyclohexyl
trans/trans-4-[2-p-(trans-4-pentylcyclohexyl)-phenylethyl]-4'-ethyl-bicyclohexyl
trans/trans-4-[2-p-(trans-4-pentylcyclohexyl)-phenylethyl]-4'-propyl-bicyclohexyl
trans/trans-4-[2-p-(trans-4-pentylcyclohexyl)-phenylethyl]-4'-butyl-bicyclohexyl
trans/trans-4-[2-p-(trans-4-pentylcyclohexyl)-phenylethyl]-4'-pentyl-bicyclohexyl
trans/trans-4-[2-p-(trans-4-pentylcyclohexyl)-phenylethyl]-4'-hexyl-bicyclohexyl
trans/trans-4-[2-p-(trans-4-pentylcyclohexyl)-phenylethyl]-4'-heptyl-bicyclohexyl
trans/trans-4-[2-p-(trans-4-hexylcyclohexyl)-phenylethyl]-4'-ethyl-bicyclohexyl
trans/trans-4-[2-p-(trans-4-hexylcyclohexyl)-phenylethyl]-4'-propyl-bicyclohexyl
trans/trans-4-[2-p-(trans-4-hexylcyclohexyl)-phenylethyl]-4'-butyl-bicyclohexyl
trans/trans-4-[2-p-(trans-4-hexylcyclohexyl)-phenylethyl]-4'-pentyl-bicyclohexyl
trans/trans-4-[2-p-(trans-4-hexylcyclohexyl)-phenylethyl]-4'-hexyl-bicyclohexyl
trans/trans-4-[2-p-(trans-4-hexylcyclohexyl)-phenylethyl]-4'-heptyl-bicyclohexyl
trans/trans-4-[2-p-(trans-4-heptylcyclohexyl)-phenylethyl]-4'-ethyl-bicyclohexyl
trans/trans-4-[2-p-(trans-4-heptylcyclohexyl)-phenylethyl]-4'-propyl-bicyclohexyl
trans/trans-4-[2-p-(trans-4-heptylcyclohexyl)-phenylethyl]-4'-butyl-bicyclohexyl
trans/trans-4-[-2-p-(trans-4-heptylcyclohexyl)-phenylethyl]-4'-pentyl-bicyclohexyl
trans/trans-4-[2-p-(trans-4-heptylcyclohexyl)-phenylethyl]-4'-hexyl-bicyclohexyl and
trans/trans-4-[2-p-(trans-4-heptylcyclohexyl)-phenylethyl]-4'-heptyl-bicyclohexyl.

EXAMPLE 2

A solution of 39.6 g of trans/trans-4-p-propylbenzoylmethyl-4'-pentyl-bicyclohexyl (obtainable from trans/trans-4'-pentyl-bicyclohexyl-4-acetyl chloride and propylbenzene/AlCl$_3$) in 500 ml of ethyl acetate is hydrogenated on 5 g of 10% Pd-on-charcoal at 20° under 5 bar. The mixture is filtered and the filtrate is evaporated to give trans/trans-4-(2-p-propylphenyl-ethyl)-4'-pentyl-bicyclohexyl.

The other compounds mentioned in Example 1 are also obtainable analogously.

EXAMPLE 3

A solution of 34 g of 1-(2-p-methoxyphenyl-ethyl)-4-(trans-4-propylcyclohexyl)-cyclohexene [obtainable by reaction of 2-p-methoxyphenyl-ethyl-magnesium bromide with 4-(trans-4-propylcyclohexyl)-cyclohexanone and subsequent hydrolysis to 1-(2-p-methoxyphenyl-ethyl)-4-(trans-4-propylcyclohexyl)-cyclohexanol and dehydration with p-toluenesulfonic acid in boiling toluene] in 600 ml of THF is hydrogenated on 5 g of PdO at 40° under 1 bar until the reaction stops. The mixture is filtered, the filtrate is evaporated, the residue is taken up in 200 ml of boiling methanol and the resulting hot solution is poured into a boiling solution of 70 g of thiourea in 300 ml of methanol. The mixture is cooled to 0° and the thiourea-inclusion compound precipitated is filtered off and boiled up with 350 ml of petroleum ether (boiling point 40°–60°). The undissolved residue is warmed at 50° with 350 ml of 2N aqueous potassium hydroxide solution for 30 minutes. The resulting solution is acidified with 10% H$_2$SO$_4$ and the trans/trans-4-

(2-p-methoxyphenyl-ethyl)-4'-propyl-bicyclohexyl which has precipitated is filtered off.

The other compounds mentioned in Example 1 are also obtainable analogously.

EXAMPLE 4

A mixture of 36.3 g of trans/trans-4-(2-p-cyanophenyl-vinyl)-4'-pentyl-bicyclohexyl (obtainable by a Wittig reaction from 4-bromomethyl-4'-pentyl-bicyclohexyl and p-cyanobenzaldehyde), 3.7 g of NaBH$_4$ and 350 ml of methanol is boiled for 4 hours. After customary working up, trans/trans-4-(2-p-cyanophenyl-ethyl)-4'-pentyl-bicyclohexyl is obtained.

The following compounds are obtained analogously, by reduction of the corresponding vinyl compounds:
trans/trans-4-(2-p-cyanophenyl-ethyl)-4'-ethyl-bicyclohexyl
trans/trans-4-(2-p-cyanophenyl-ethyl)-4'-propyl-bicyclohexyl
trans/trans-4-(2-p-cyanophenyl-ethyl)-4'-butyl-bicyclohexyl
trans/trans-4-(2-p-cyanophenyl-ethyl)-4'-hexyl-bicyclohexyl and
trans/trans-4-(2-p-cyanophenyl-ethyl)-4'-heptyl-bicyclohexyl.

EXAMPLE 5

35.6 g of p-[2-(trans/trans-4'-propyl-bicyclohexyl-4-yl)-ethyl]-benzoic acid (obtainable by a Wittig reaction from trans/trans-4-bromomethyl-4'-propyl-bicyclohexyl and terephthalaldehydic acid to give p-[2-(trans/trans-4'-propylbicyclohexyl-4-yl)-vinyl]-benzoic acid and hydrogenation) are boiled with 24 g of SOCl$_2$ for 1 hour, the mixture is evaporated, the resulting crude acid chloride is dissolved in 300 ml of toluene, 8 ml of pyridine and 13 g of (−)-2-octanol are added and the mixture is boiled for 2 hours. After cooling and customary working up, (−)-2-octyl p-[2-(trans/trans-4'-propyl-bicyclohexyl-4-yl)-ethyl]-benzoate is obtained.

The following compounds are obtainable by esterification:
Ethyl p-[2-(trans/trans-4'-ethyl-bicyclohexyl-4-yl)-ethyl]-benzoate
Propyl p-[2-(trans/trans-4'-ethyl-bicyclohexyl-4-yl)-ethyl]-benzoate
Butyl p-[2-(trans/trans-4'-ethyl-bicyclohexyl-4-yl)-ethyl]-benzoate
Ethyl p-[2-(trans/trans-4'-propyl-bicyclohexyl-4-yl)-ethyl]-benzoate
Propyl p-[2-(trans/trans-4'-propyl-bicyclohexyl-4-yl)-ethyl]-benzoate
Butyl p-[2-(trans/trans-4'-propyl-bicyclohexyl-4-yl)-ethyl]-benzoate
Ethyl p-[2-(trans/trans-4'-butyl-bicyclohexyl-4-yl)-ethyl]-benzoate
Propyl p-[2-(trans/trans-4'-butyl-bicyclohexyl-4-yl)-ethyl]-benzoate
Butyl p-[2-(trans/trans-4'-butyl-bicyclohexyl-4-yl)-ethyl]-benzoate
Ethyl p-[2-(trans/trans-4'-pentyl-bicyclohexyl-4-yl)-ethyl]-benzoate
Propyl p-[2-(trans/trans-4'-pentyl-bicyclohexyl-4-yl)-ethyl]-benzoate
Butyl p-[2-(trans/trans-4'-pentyl-bicyclohexyl-4-yl)-ethyl]-benzoate
Ethyl p-[2-(trans/trans-4'-hexyl-bicyclohexyl-4-yl)-ethyl]-benzoate
Propyl p-[2-(trans/trans-4'-hexyl-bicyclohexyl-4-yl)-ethyl]-benzoate
Butyl p-[2-(trans/trans-4'-hexyl-bicyclohexyl-4-yl)-ethyl]-benzoate
Ethyl p-[2-(trans/trans-4'-heptyl-bicyclohexyl-4-yl)-ethyl]-benzoate
Propyl p-[2-(trans/trans-4'-heptyl-bicyclohexyl-4-yl)-ethyl]-benzoate and
Butyl p-[2-(trans/trans-4'-heptyl-bicyclohexyl-4-yl)-ethyl]-benzoate.

EXAMPLE 6

32.8 g of trans/trans-4-(2-p-hydroxyphenylethyl)-4'-propyl-bicyclohexyl and 30 g of CH$_3$COONa in 100 ml of acetic anhydride are heated at 80° for 1 hour and the mixture is cooled and worked up in the customary manner to give trans/trans-4-(2-p-acetoxyphenylethyl)-4'-propylbicyclohexyl.

The following compounds are obtained analogously by esterification:
trans/trans-4-(2-p-acetoxyphenylethyl)-4'-ethyl-bicyclohexyl
trans/trans-4-(2-p-acetoxyphenylethyl)-4'-butyl-bicyclohexyl
trans/trans-4-(2-p-acetoxyphenylethyl)-4'-pentyl-bicyclohexyl
trans/trans-4-(2-p-acetoxyphenylethyl)-4'-hexyl-bicyclohexyl
trans/trans-4-(2-p-acetoxyphenylethyl)-4'-heptyl-bicyclohexyl
trans/trans-4-(2-p-propionyloxyphenylethyl)-4'-ethyl-bicyclohexyl
trans/trans-4-(2-p-propionyloxyphenylethyl)-4'-propyl-bicyclohexyl
trans/trans-4-(2-p-propionyloxyphenylethyl)-4'-butyl-bicyclohexyl
trans/trans-4-(2-p-propionyloxyphenylethyl)-4'-pentyl-bicyclohexyl
trans/trans-4-(2-p-propionyloxyphenylethyl)-4'-hexyl-bicyclohexyl
trans/trans-4-(2-p-propionyloxyphenylethyl)-4'-heptyl-bicyclohexyl
trans/trans-4-(2-p-butyryloxyphenylethyl)-4'-ethyl-bicyclohexyl
trans/trans-4-(2-p-butyryloxyphenylethyl)-4'-propyl-bicyclohexyl
trans/trans-4-(2-p-butyryloxyphenylethyl)-4'-butyl-bicyclohexyl
trans/trans-4-(2-p-butyryloxyphenylethyl)-4'-pentyl-bicyclohexyl
trans/trans-4-(2-p-butyryloxyphenylethyl)-4'-hexyl-bicyclohexyl and
trans/trans-4-(2-p-butyryloxyphenylethyl)-4'-heptyl-bicyclohexyl.

EXAMPLE 7

180 ml of 35% aqueous tetrafluoboric acid solution are added to a suspension of 39.7 g of trans/trans-4-[2-(3-amino-4-propylphenyl)-ethyl]-4'-pentyl-bicyclohexyl (obtainable by nitration of trans/trans-4-p-propylbenzoylmethyl-4'-pentyl-bicyclohexyl and subsequent hydrogenation of the resulting crude B 3-nitro compound on Pd in THF) in 180 ml of dioxane at 15°-20°, with stirring, and a solution of 7.2 g of NaNO$_2$ in 25 ml of water is then added dropwise at 0°. The mixture is subsequently stirred for 6 hours, during which the temperature is allowed to rise to 15°. After customary working up (extraction with toluene, filtration over silica gel), trans/trans-4-[2-(3-fluoro-4-propyl-phenyl)-ethyl]-4'-pentyl-bicyclohexyl is obtained.

The following compounds can be obtained analogously from the coresponding amino compounds:
trans/trans-4-(2-o-fluorophenyl-ethyl)-4'-propyl-bicyclohexyl
trans/trans-4-(2-p-fluorophenyl-ethyl)-4'-ethyl-bicyclohexyl
trans/trans-4-(2-p-fluorophenyl-ethyl)-4'-propyl-bicyclohexyl
trans/trans-4-(2-p-fluorophenyl-ethyl)-4'-butyl-bicyclohexyl
trans/trans-4-(2-p-fluorophenyl-ethyl)-4'-pentyl-bicyclohexyl
trans/trans-4-(2-p-fluorophenyl-ethyl)-4'-hexyl-bicyclohexyl and
trans/trans-4-(2-p-fluorophenyl-ethyl)-4'-heptyl-bicyclohexyl.

EXAMPLE 8

A solution of 7.2 g of $NaNO_2$ in 25 ml of water is added to a suspension of 35.5 g of trans/trans-4-(2-p-aminophenyl-ethyl)-4'-pentyl-bicyclohexyl [obtainable by nitration of trans/trans-4-(2-phenylethyl)-4'-pentyl-bicyclohexyl to 4-(2-p-nitrophenyl-ethyl)-4'-pentyl-bicyclohexyl and hydrogenation on Pd] in 150 ml of 15% aqueous hydrobromic acid at $-5°$ in the course of 0.5 hour. The solution thus obtained is added dropwise, at 0°–5° in the course of 1 hour, to a Cu(I) salt solution which has been prepared from 25 g of copper sulfate, 15.4 g of NaBr, 6.3 g of $Na_2SO_3$, 100 ml of water and 40 ml of 32% hydrobromic acid. After the mixture has been heated to 40° for half an hour, it is extracted with $CH_2Cl_2$ and the extract is worked up in the customary manner. Trans/trans-4-(2-p-bromophenyl-ethyl)-4'-pentyl-bicyclohexyl is obtained.

The following compounds are obtainable analogously from the corresponding amino compounds by a Sandmeyer reaction:
trans/trans-4-(2-p-chlorophenyl-ethyl)-4'-ethyl-bicyclohexyl
trans/trans-4-(2-p-chlorophenyl-ethyl)-4'-propyl-bicyclohexyl
trans/trans-4-(2-p-chlorophenyl-ethyl)-4'-butyl-bicyclohexyl
trans/trans-4-(2-chlorophenyl-ethyl)-4'-pentyl-bicyclohexyl
trans/trans-4-(2-p-chlorophenyl-ethyl)-4'-hexyl-bicyclohexyl
trans/trans-4-(2-p-chlorophenyl-ethyl)-4'-heptyl-bicyclohexyl
trans/trans-4-(2-p-bromophenyl-ethyl)-4'-ethyl-bicyclohexyl
trans/trans-4-(2-p-bromophenyl-ethyl)-4'-propyl-bicyclohexyl
trans/trans-4-(2-p-bromophenyl-ethyl)-4'-butyl-bicyclohexyl
trans/trans-4-(2-p-bromophenyl-ethyl)-4'-hexyl-bicyclohexyl and
trans/trans-4-(2-p-bromophenyl-ethyl)-4'-heptyl-bicyclohexyl.

EXAMPLE 9

A solution of 45.7 g of trans/trans-4-[2-p-(trans-4-chlorocarbonylcyclohexyl)-phenyl-ethyl]-4'-propyl-bicyclohexyl and 8 g of sulfamide in 500 ml of tetramethylene sulfone is heated at 120° for 4 hours and evaporated and the residue is worked up in the customary manner. Trans/trans-4-[2-p-(trans-4-cyanocyclohexyl)-phenyl-ethyl]-4'-propyl-bicyclohexyl is obtained.

The following compounds are obtained analogously from the corresponding acid chlorides:
trans/trans-4-[2-p-(trans-4-cyanocyclohexyl)-phenylethyl]-4'-ethyl-bicyclohexyl
trans/trans-4-[2-p-(trans-4-cyanocyclohexyl)-phenylethyl]-4'-butyl-bicyclohexyl
trans/trans-4-[2-p-(trans-4-cyanocyclohexyl)-phenylethyl]-4'-pentyl-bicyclohexyl
trans/trans-4-[2-p-(trans-4-cyanocyclohexyl)-phenylethyl]-4'-hexyl-bicyclohexyl
trans/trans-4-[2-p-(trans-4-cyanocyclohexyl)-phenylethyl]-4'-heptyl-bicyclohexyl
trans/trans-4-[2-(trans/trans-4'-cyanobicyclohexyl-4-yl)-ethyl]-4'-ethyl-bicyclohexyl
trans/trans-4-[2-(trans/trans-4'-cyanobicyclohexyl-4-yl)-ethyl]-4'-propyl-bicyclohexyl
trans/trans-4-[2-(trans/trans-4'-cyanobicyclohexyl-4-yl)-ethyl]-4'-butyl-bicyclohexyl
trans/trans-4-[2-(trans/trans-4'-cyanobicyclohexyl-4-yl)-ethyl]-4'-pentyl-bicyclohexyl
trans/trans-4-[2-(trans/trans-4'-cyanobicyclohexyl-4-yl)-ethyl]-4'-hexyl-bicyclohexyl and
trans/trans-4-[2-(trans/trans-4'-cyanobicyclohexyl-4-yl)-ethyl]-4'-heptyl-bicyclohexyl.

EXAMPLE 10

A mixture of 41.9 g of trans/trans-4-(2-p-bromophenyl-ethyl)-4'-pentyl-bicyclohexyl, 10 g of $Cu_2(CN)_2$, 120 ml of pyridine and 60 ml of N-methylpyrrolidone is heated at 150° for 2 hours. The mixture is cooled, a solution of 120 g of iron(III) chloride hexahydrate in 600 ml of 20% hydrochloric acid is added and the mixture is warmed at 70° for 1.5 hours, with stirring, and worked up in the customary manner to give trans/trans-4-(2-p-cyanophenyl-ethyl)-4'-pentyl-bicyclohexyl.

The nitriles mentioned in Examples 4, 9 and 10 are obtainable analogously, as well as
trans/trans-4-[2-(2-cyano-4-propylphenyl)-ethyl]-4'-propyl-bicyclohexyl
trans/trans-4-[2-(2-3-difluoro-4-cyanophenyl)-ethyl]-4'-propyl-bicyclohexyl and
trans/trans-4-[2-(2-methyl-4-cyanophenyl)-ethyl]-4'-propyl-bicyclohexyl.

EXAMPLE 11

A mixture of 35.6 g of trans/trans-4-(2-p-hydroxyphenyl-ethyl)-4'-pentyl-bicyclohexyl (obtainable by a Wittig reaction from trans/trans-4-bromomethyl-4'-pentyl-bicyclohexyl and p-hydroxybenzaldehyde to give trans/trans-4-(2-p-hydroxyphenyl-vinyl)-4'-pentyl-bicyclohexyl and hydrogenation), 6.9 g of $K_2CO_3$, 25 g of hexyl iodide and 250 ml of DMF is heated at 80° for 16 hours, with stirring, and the mixture is then cooled and worked up in the customary manner. Trans/trans-4-(2-p-hexoxyphenyl-ethyl)-4'-pentyl-bicyclohexyl is obtained.

The ethers mentioned in Example 1 are obtained analogously by etherification, as well as the following compounds:
trans/trans-4-(2-p-pentoxyphenyl-ethyl)-4'-propyl-bicyclohexyl
trans/trans-4-(2-p-pentoxyphenyl-ethyl)-4'-butyl-bicyclohexyl
trans/trans-4-(2-p-pentoxyphenyl-ethyl)-4'-pentyl-bicyclohexyl trans/trans-4-(2-p-hexoxyphenyl-ethyl)-4'-propyl-bicyclohexyl trans/trans-4-(2-p-hexoxyphenyl-ethyl)-4'-butyl-bicyclohexyl trans/trans-4-(2-p-hexoxyphenyl-ethyl)-4'-pentyl-bicyclohexyl trans/trans-4-(2-p-heptoxyphenyl-ethyl)-4'-propyl-bicyclohexyl trans/trans-4-(2-p-heptoxyphenyl-ethyl)-4'-butyl-bicyclohexyl trans/trans-4-(2-p-heptoxyphenyl-ethyl)-4'-pentyl-bicyclohexyl trans/trans-4-(2-p-octoxyphenyl-ethyl)-4'-propyl-bicyclohexyl trans/trans-4-(2-p-octoxyphenyl-ethyl)-4'-butyl-bicyclohexyl trans/trans-4-(2-p-octoxyphenyl-ethyl)-4'-pentyl-bicyclohexyl trans/trans-4-(2-p-nonoxyphenyl-ethyl)-4'-propyl-bicyclohexyl trans/trans-4-(2-p-nonoxyphenyl-ethyl)-4'-butyl-bicyclohexyl trans/trans-4-(2-p-nonoxyphenyl-ethyl)-4'-pentyl-bicyclohexyl trans/trans-4-(2-p-decoxyphenyl-ethyl)-4'-propyl-bicyclohexyl trans/trans-4-(2-p-decoxyphenyl-ethyl)-4'-butyl-bicyclohexyl and trans/trans-4-(2-p-decoxyphenyl-ethyl)-4'-pentyl-bicyclohexyl.

The following examples relate to dielectrics according to the invention containing at least one compound of the formula I:

EXAMPLE A

Addition of trans/trans-4-(2-p-propylphenyl-ethyl)-4'-propyl-bicyclohexyl ("A") increases the clear point of a mixture ("M") of 29% of p-trans-4-propylcyclohexyl-benzonitrile, 41% of p-trans-4-pentylcyclohexyl-benzonitrile and 30% of p-trans-4-heptylcyclohexyl-benzonitrile as follows:

| | |
|---|---|
| 100% "M" | c.p. 52° |
| 90% "M" + 10% "A" | c.p. 61° |
| 80% "M" + 20% "A" | c.p. 70° |
| 70% "M" + 30% "A" | c.p. 79°. |

EXAMPLE B

Addition of "A" increases the clear point of a mixture ("N") of 24% of p-trans-4-propylcyclohexyl-benzonitrile, 36% of p-trans-4-pentylcyclohexyl-benzonitrile, 25% of p-trans-4-heptylcyclohexyl-benzonitrile and 15% of 4-cyano-4'-(trans-4-pentylcyclohexyl)-biphenyl as follows:

| | |
|---|---|
| 100% "N" | c.p. 71° |
| 90% "N" + 10% "A" | c.p. 78° |
| 80% "N" + 20% "A" | c.p. 85° |
| 70% "N" + 30% "A" | c.p. 93°. |

EXAMPLE C

A mixture of
17% of "A"
15% of p-trans-4-propylcyclohexyl-benzonitrile
27% of trans-1-p-ethylphenyl-4-propylcyclohexane
10% of trans-2-p-ethoxyphenyl-4-propylcyclohexane
7% of 4-cyano-4'-(trans-4-pentylcyclohexyl)-biphenyl
10% of 4-(trans-4-pentylcyclohexyl)-4'-(trans-4-propylcyclohexyl)-biphenyl
8% of p-propylphenyl p-trans-4-propylcyclohexyl-benzoate and
6% of p-propylphenyl p-trans-4-pentylcyclohexyl-benzoate has a c.p. of 85°.

EXAMPLE D

A mixture of
19% of "A"
15% of p-trans-4-propylcyclohexyl-benzonitrile
12% of p-trans-4-butylcyclohexyl-benzonitrile
14% of trans-1-p-ethylphenyl-4-propylcyclohexane
10% of trans-1-p-ethoxyphenyl-4-propylcyclohexane
6% of 4-cyano-4'-(trans-4-pentylcyclohexyl)-biphenyl
4% of 4,4'-bis-(trans-4-propylcyclohexyl)-biphenyl
6% of 4-(trans-4-pentylcyclohexyl)-4'-(trans-4-propylcyclohexyl)-biphenyl
8% of p-propylphenyl p-trans-4-propylcyclohexyl-benzoate and
6% of p-propylphenyl p-trans-4-pentylcyclohexyl-benzoate has a c.p. of 100°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A bicyclohexylethane of the formula

$$R^1-Cy-Cy-CH_2CH_2-A-(Cy)_n-R^2$$

wherein $R^1$ is alkyl; $R^2$ is alkyl, alkyl in which one or two non-adjacent $CH_2$ groups are replaced by 0 atoms, or is —COOalkyl or —O—CO-alkyl; or one of $R^1$ or $R^2$ can also be H; A is Cy or 1,4-phenylene (Phe); Cy is 1,4-cyclohexylene; and n is 0 or 1; the alkyl groups in each case containing 1-10 C atoms.

2. A compound of claim 1 of the formula $R^1$—Cy—Cy—$CH_2CH_2$—Cy—$R^2$.

3. A compound of claim 1 of the formula $R^2$—Cy—Cy—$CH_2CH_2$—Phe—$R^2$.

4. A compound of claim 1 of the formula $R^1$—Cy—Cy—$CH_2CH_2$—Cy—Cy—$R^2$.

5. A compound of claim 1 of the formula $R^1$—Cy—Cy—$CH_2CH_2$—Phe—Cy—$R^2$.

6. A compound of claim 1, wherein all alkyl groups are straight chained.

7. A compound of claim 1, wherein $R^2$ is alkyl, or alkoxy.

8. A compound of claim 1, wherein A is Cy.

9. A compound of claim 1, wherein n is 0.

10. A compound of claim 1 of the formula
$R^1$—Cy—Cy—$CH_2CH_2$—Cy—alkyl
$R^1$—Cy—Cy—$CH_2CH_2$—Phe—alkyl, or
$R^1$—Cy—Cy—$CH_2CH_2$—Phe—alkoxy.

11. A liquid crystal dielectric comprising at least two liquid crystalline components wherein at least one is a bicyclohexylethane of claim 1.

12. A dielectric of claim 11 comprising 2-15 components.

13. A dielectric of claim 11, wherein the amount of said bicyclohexylethane is 1-60 wt %.

14. In an electrooptical display element, comprising a liquid crystalline dielectric, the improvement wherein the dielectric is that of claim 11.

* * * * *